(12) United States Patent
Fleury

(10) Patent No.: US 7,221,165 B2
(45) Date of Patent: May 22, 2007

(54) METHOD AND DEVICE FOR MEASURING THE RESISTIVITY ANISOTROPY OF LAYERED ROCK SAMPLES

(75) Inventor: Marc Fleury, La Celle Saint Cloud (FR)

(73) Assignee: Institut Francais Du Petrole, Cedex (FR)

( * ) Notice: Subject to any disclaimer, the term of this patent is extended or adjusted under 35 U.S.C. 154(b) by 237 days.

(21) Appl. No.: 10/961,085

(22) Filed: Oct. 12, 2004

(65) Prior Publication Data

US 2005/0104596 A1   May 19, 2005

(30) Foreign Application Priority Data

Oct. 10, 2003   (FR) .................................. 03 11958

(51) Int. Cl.
*G01R 27/04* (2006.01)
(52) U.S. Cl. ..................................... 324/376
(58) Field of Classification Search ................. 324/376
See application file for complete search history.

(56) References Cited

U.S. PATENT DOCUMENTS

| 4,686,477 | A | | 8/1987 | Givens et al. | |
|---|---|---|---|---|---|
| 4,924,187 | A | * | 5/1990 | Sprunt et al. | ............... 324/376 |
| 4,926,128 | A | * | 5/1990 | Givens | ........................ 324/376 |
| 5,093,623 | A | * | 3/1992 | Givens et al. | ............... 324/376 |
| 5,105,154 | A | | 4/1992 | Givens et al. | |
| 5,610,524 | A | * | 3/1997 | Longeron et al. | ............ 324/376 |
| 6,229,312 | B1 | * | 5/2001 | Fleury et al. | ................ 324/376 |
| 2001/0046811 | A1 | | 11/2001 | Fleury et al. | |

* cited by examiner

*Primary Examiner*—Reena Aurora
(74) *Attorney, Agent, or Firm*—Antonelli, Terry, Stout & Kraus, LLP

(57) ABSTRACT

A method and device with application to petrophysical measurements on porous rocks for measuring the resistivity anisotropy of rocks exhibiting layerings of different conductivity such as laminations is disclosed. The method comprises setting a sample saturated with a first fluid into a petrophysical measurement device allowing the sample to be subjected to drainage operations by injection under pressure of a second fluid. At least one pressure injection is established for the second fluid, and continuous and precise measurements of the variations in the complex electrical impedance of the sample at several frequencies are performed during a displacement of the saturating fluid. Measurements of the impedance exhibited by the sample in a position where the layerings are oriented substantially transverse to the electrical field (EF) created by applying the electric current are performed and then the same measurements are performed where the layerings are oriented substantially in the direction of the electrical field. The resistivity anisotropy is then determined.

16 Claims, 3 Drawing Sheets

$R = \Delta U/l$ $R = \Delta U/l$ lamination $R = \Delta U / l$

METHOD AND DEVICE FOR MEASURING THE RESISTIVITY ANISOTROPY OF LAYERED ROCK SAMPLES

BACKGROUND OF THE INVENTION

1. Field of the Invention

The present invention relates to a method and a device for measuring the resistivity anisotropy of rocks exhibiting layerings such as laminations. This layering is due to the existence of clay layers or of compacted sand beds of different grain sizes. When the formation is 100% water saturated, the resistivity contrast is low (factor 3 for example). But in oil zones, this contrast is very high because of a very different water saturation.

Measurement of the resistivity index of core samples exhibiting such layerings is necessary to obtain a precise estimation of the water saturation from log data obtained for example by means of the measuring while drilling (MWD technique).

Knowledge of the resistivity anisotropy in two preferred directions is useful to determine the water saturation of the porous medium present between the laminations. In fact, the vertical resolution of well logging tools is often insufficient to detect the resistivity fluctuations resulting from the accumulation of the various layerings according to the depth. Furthermore, the laminations contain few hydrocarbons and can be of very low permeability because they often essentially consist of clay. Thus, it is well-known that measurement of the mean resistivity in a direction does not allow determination of the water saturation in the layers that can produce hydrocarbons.

2. Description of the Prior Art

EP-701,128 (U.S. Pat. No. 5,610,524) and French patent 2,581,573 (U.S. Pat. No. 5,979,223) filed by the assignee describe various methods and devices intended for continuous measurement of the curve of the resistivity index of a solid sample initially saturated with a first wetting fluid, such as a geologic sample, independently of the capillary pressure curve. The porous solid sample is contained in a sealed sheath placed in an elongate containment cell between two terminal parts. Channels through both terminal parts communicate with an injection system allowing injection of a second, non-wetting fluid into the sample at a first end of the cell and draining of the first fluid out of the cell at the opposite end, through a semipermeable membrane permeable to the first fluid. The sample is contained in a sheath and subjected to a radial pressure by injection of oil under pressure into the annular space between the body of the cell and the sheath. A membrane wettable only by the second fluid is interposed between the sample and the first end of the cell to carry out re-imbibition operations.

Electrodes interposed between the sample and the sample sheath allow application of an electric current and detection of the potential differences that appear between distinct points in response to the application of the electric current. The electrodes are connected to a device measuring the complex impedance of the sample. The longitudinal extension of the electrodes is relatively great in relation to the length of the sample so as to involve the largest possible part of the volume of the sample in the impedance measurements while avoiding short-circuits through the ends of the sample likely to distort the measurements.

One or more injection pressure stages are applied and the continuous variations of the resistivity index as a function of the mean saturation variation are measured without waiting for the capillary equilibria to be established.

Since the annular space between the sheath and the outer wall of the cell are under high pressure, the electric conductors connecting the electrodes to the measuring device run through the outer wall of the cell through sealed ducts (glass bead connectors for example).

In order to improve the measuring accuracy when operating at much higher frequencies in the 100 kHz–10 MHz range for example, it is possible to advantageously use the connection device described in French patent 2,809,821 (U.S. Pat. No. 6,571,606) filed by the assignee, which allows a shielded cable connection of the electrodes to a measuring device, located on either side of a wall separating an enclosure under pressure from the outside medium.

SUMMARY OF THE INVENTION

The method according to the invention allows measurement of the resistivity anisotropy of a porous sample traversed by at least one layering of different conductivity, such as a lamination, this sample being initially saturated with a first fluid. The method comprises setting the sample in a device comprising an elongate containment cell, with a first semipermeable filter permeable to the first fluid and arranged substantially in contact with a first end of the sample, and means for injecting under pressure a second fluid through a second end of the sample, the application of electrodes against the sample allowing application of an electric current and detection of the potential differences that appear between distinct application points in response to the application of the electric current, establishing at least one injection pressure stage for the second fluid and carrying out continuous precise measurements of the variations in the complex electric impedance of the sample at several frequencies during a displacement stage of the saturating fluid.

The method comprises:

a) carrying out measurements of the impedance of the sample in a position where the layering(s) are oriented substantially transverse to the electric field created by applying the electric current;

b) carrying out measurements of the impedance of the sample in a position where the layerings are oriented substantially in the direction of the electric field created by applying the electric current; and c) determining the resistivity anisotropy.

According to a first implementation mode, the orientation of the sample in relation to the fixed direction of the electric field created by applying the electric current is changed prior to carrying out stage b) so that the layering is substantially in the same direction as the electric field.

According to another implementation mode, the direction of the electric field created by applying the electric current in relation to the sample is changed prior to carrying out stage b).

Electrodes, whose length ranges between ¼ and ¾ of the length of the sample and for example of the order of half the length of the sample, can be used.

According to an implementation mode, continuous precise measurements of the variations in the complex electric impedance of the sample at several frequencies during a drainage stage are performed.

According to an implementation mode, continuous precise measurements of the variations in the complex electric impedance of the sample at several frequencies during an imbibition stage are performed.

The device according to the invention allows measurement of the resistivity anisotropy of a porous sample crossed through by at least one layering of different conductivity, such as a lamination, comprising a containment cell for a sample initially saturated with a first fluid, pairs of electrodes pressed against the periphery of the sample allowing application of an electric current and detection of the potential differences that appear between distinct points of the sample in response to the application of the electric current, the electrodes being connected to a device for measuring the impedance of the sample, a first semipermeable filter permeable to the first fluid and arranged substantially in contact with a first end of the sample, and injection means for injecting under pressure a second fluid through a second end of the sample.

The device comprises a plurality of pairs of electrodes distributed over the periphery of the sample, which can be selectively connected to the measuring device so as to position the electric field created by applying the electric current to the sample respectively in the same direction as the layering, in stage b) substantially, and in a transverse direction to this layer in stage a).

BRIEF DESCRIPTION OF THE DRAWINGS

Other features and advantages of the invention will be clear from reading the description hereafter of a non-limitative embodiment example, with reference to the accompanying drawings wherein.

DETAILED DESCRIPTION OF THE INVENTION

Figure 1:
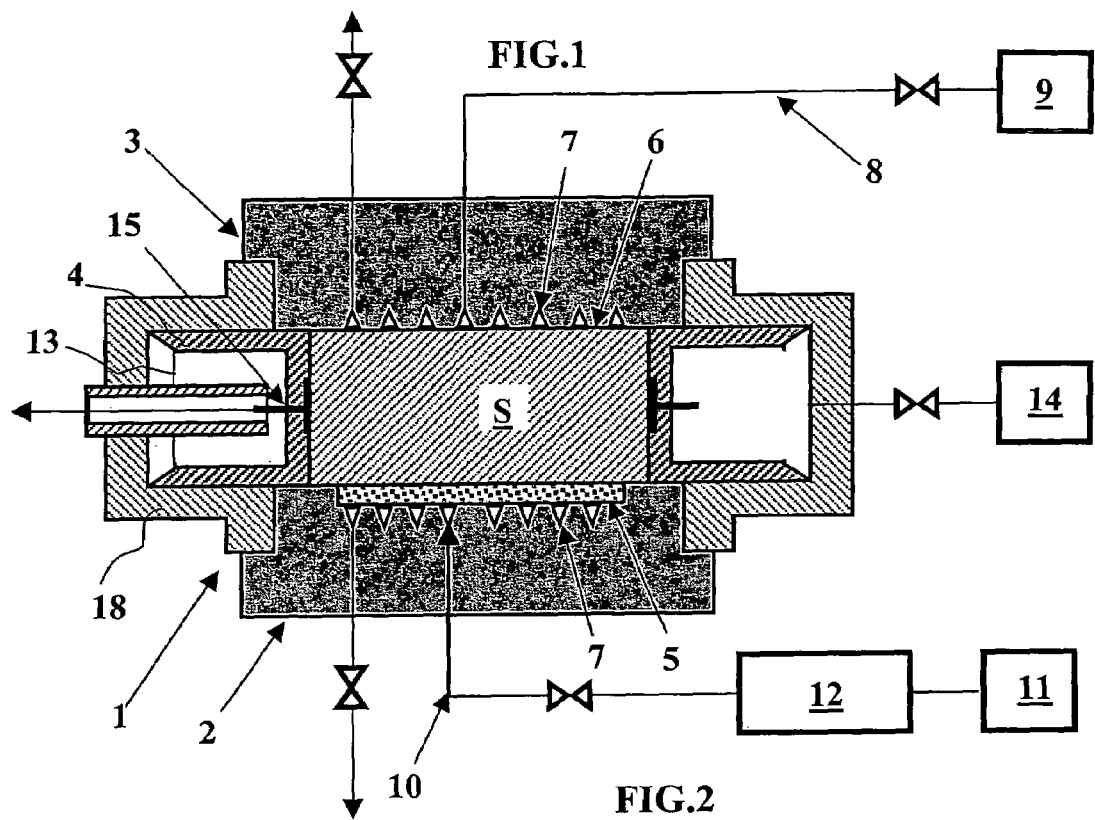
FIG. 1 diagrammatically shows, in longitudinal section, a measuring cell allowing the resistivity of a porous sample to be measured.
Figure 2:
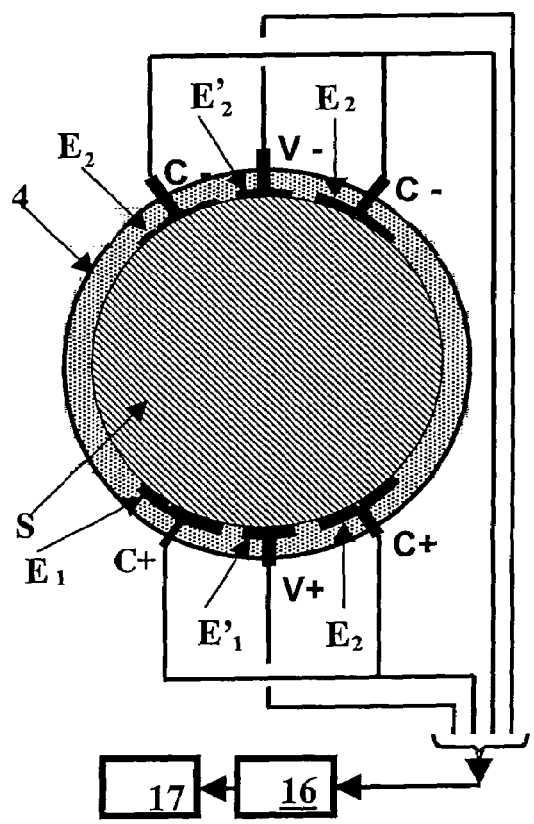
FIG. 2 shows, in cross section, the layout of the electrodes around a sample allowing application of an electric current and detection of the potential difference generated by the current getting through the sample.

The method according to the invention can be implemented by an experimental system intended for measurement of the variations in the resistivity index of a porous solid sample, resulting from forced displacements of a first electricity-conducting wetting fluid such as brine, for example, by injection of a second, non-conducting fluid such as oil, for example (drainage stage), or of the second fluid by the first fluid (imbibition stage) as described in the aforementioned patents filed by the assignee. The method comprises for example (FIG. 1) a containment cell for a core sample, comprising a hollow body 1 of cylindrical symmetry, closed at its two opposite ends by two terminal parts 2, 3. Sample S is placed inside an elastomer cylindrical part 4 whose longitudinal section is U-shaped, forming a sheath for sample S. The assembly made up of sample S and sheath 4 is installed in an inner cavity of body 1 and is axially limited, on either side, by the two terminal parts 2, 3. On the side of terminal part 2, sample S is in contact with a semipermeable filter 5 wettable by the first fluid, such as a ceramic filter. On the opposite side of terminal part 3, sample S is in contact with a membrane 6 wettable by the second fluid. The inner faces of the two terminal parts 2, 3 are provided with a network of grooves 7 (FIG. 2). Fastening means (not shown) allow the two terminal parts to be tightly fastened to one another.

Channels 8 run through terminal part 3 and communicate with the network of grooves 7, on the terminal face thereof, with a first source 9 delivering the second fluid under pressure. Similarly, channels 10 run through terminal part 2 and communicate with the corresponding network of grooves 7 with a collection device 11 intended to recover the first fluid drained out of the sample as a result of the injection of the second fluid. An element 12 installed on circuit 9 is intended to measure the volume of fluid displaced out of sample S. A low-cost capacitive detector having a 0.05-cc precision and a 0.01-cc resolution, similar to the detector used in the device described in French patent application Patent 2,772,477 filed by the assignee, is preferably used.

The device comprises for example two pairs of electrodes E1, E2 which are cast inside sheath 4 so as to be tightly pressed against the peripheral wall of the sample, allowing an electric current to be applied. The potential difference V created in response to the application of the electric current is measured by means of another pair of electrodes E'1, E'2, similarly cast.

This separate allocation of the pairs of electrodes, one to the application of a current and the other to the measurement of potential differences, allows avoiding resistances due to contacts. The electrodes are, for example, of square shape and made of Monel. The angular extension of a pair of electrodes around the sample is below 90°. Their length has to be less than the length of the s ample so as to avoid end short-circuits exterior to the sample, directly through the fluids, which would distort the measurements. However, their length has to be great enough in relation to the length of the sample so that the current lines involve the largest part of the volume thereof with a relatively regular distribution. This length can vary in significant proportions depending on the diameter of the sample. In the experiments carried out, it has been found that the length of the electrodes can advantageously range between ¼ and ¾ of the length of the sample, and preferably be of the order of half this length.

The annular space 13 between body 1 and sheath 4 communicates with pressure means 14 allowing injection of a liquid under pressure which exerts a radial confining pressure on sample S. The radial confining pressure around the sample is for example of the order of some MPa, enough to provide good electric contact of the electrodes. Thus, under normal conditions, the contact resistance is generally of the same order as the resistance of the sample, which has to be measured with a low water saturation.

The assembly is placed in a thermostatically-controlled enclosure (not shown).

All the electrodes P are provided with a hollow extension 15 running through the thickness of sheath 4, and the electrodes are connected to an impedance meter RLC 16 coupled with a measurement acquisition device 17.

Implementation

Sample S, whose resistivity anisotropy is to be measured, is a rock bar (sandstone for example) exhibiting a layering such as a thin clay layer. This sample is saturated with a first fluid.

Figure 3A:
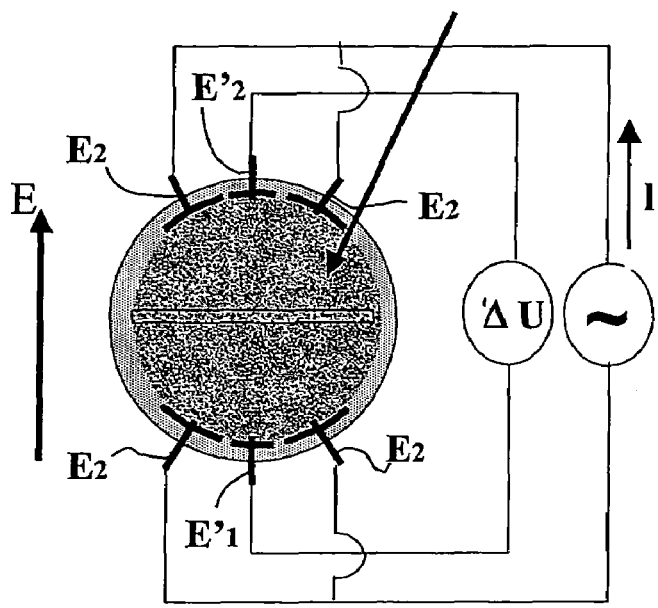
FIGS. 3A, 3B show a cross section of the sample in its containment sheath, so arranged that the layering is substantially perpendicular to the direction of the electric field established between the electrodes, in response to the application of the electric current.
Figure 3B:
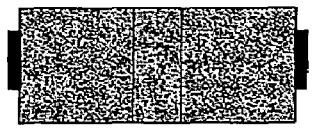

The sample S is first placed (FIGS. 3A, 3B) in sheath 4 so that the direction of extension of the layering (laminations in FIGS. 3A, B 4A, B and 5A and B) is substantially perpendicular to the electric field EP that is going to be created in the bar by applying the current between electrodes E2 and detected by electrodes E'1, E'2, and a radial confining pressure is applied by connection with a pressure source 14.

A second fluid, such as oil, is then injected through channels 8 at a first pressure and the variations in the complex impedance of the sample are continuously measured at several frequencies between 0.1 Hz and several tens of MHz, which are recorded by acquisition device 16, 17. The data are analyzed using a generalized resistivity index or impedance index which is a function of the saturation and of the frequency f, as defined below:

$$Ir(Sw) = \frac{|Z(Sw)|}{|Z(Sw=1)|} = g(Sw, f) \text{ where } |Z| = (\text{Re}(Z)^2 + \text{Im}(Z)^2)^{\frac{1}{2}}$$

Figure 4A:
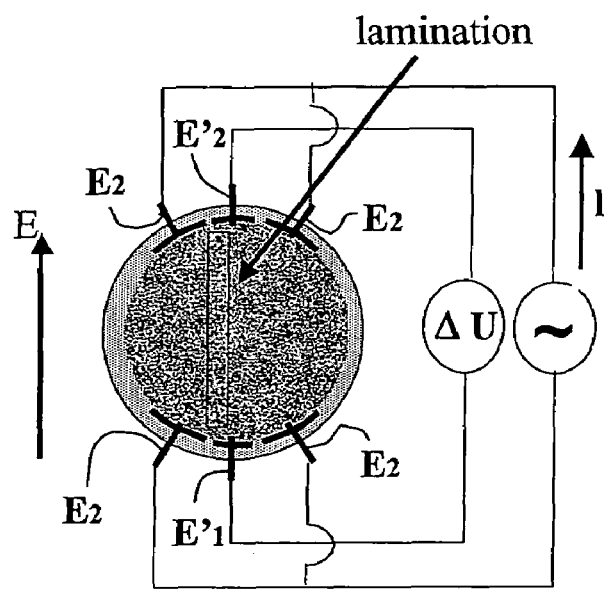
FIGS. 4A, 4B show a cross section of the same sample in its containment sheath, so arranged that the layering is substantially parallel to the direction of the electric field.
Figure 4B:

The previous operations are subsequently repeated after rotating the bar so that the layering (lamination) is now parallel to the direction of electric field EP (FIGS. 4A, 4B).

Figure 5A:
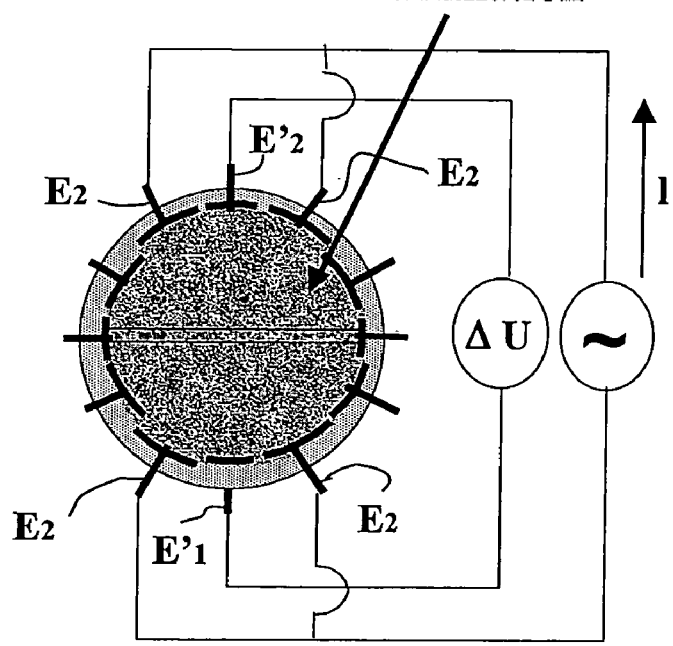
FIGS. 5A, 5B show an arrangement of several pairs of electrodes that can be selectively connected to the impedance measuring device, which allow changing the relative orientation of the layering in relation to the direction of the electric field actually getting through the sample and thus avoiding handling thereof between the measuring stages.
Figure 5B:
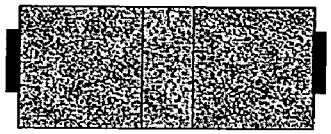

In order to save dismantling the containment cell to reach the bar so as to rotate it and to change its orientation in relation to the electric field, it is possible to use a cell with electrodes distributed all over the periphery of the bar and to selectively connect them to measuring device 16, 17 so that the electric field EP created through the bar once set in the sheath and application of the electric current is alternately perpendicular and parallel to the layering (FIGS. 5A, 5B).

Exploitation of Results

The resistivity anisotropy of the sample is deduced from the impedance measurements successively performed in the two directions.

A recent exploitation method allows, from knowledge of the resistivity anisotropy, to go back to the saturation in the hydrocarbon-producing layers. Resistivity anisotropy results for interpretation of resistivity logs are given in: "Anisotropy Of Resistivity In Oil Bearing Thin-Bedded Formations: Experiment and Modeling", Clavaud J. B. and J. Lavigne, Proceedings of the 2003 International Conference of the Society of Core Analysts, 21–24, Pau, September 2003.

Knowledge of the volume fraction of the laminations and of the resistivity anisotropy as measured in the system described allows calculation of the water saturation of layers likely to produce hydrocarbons.

The invention claimed is:

1. A method for determining resistivity anisotropy of a porous sample traversed by at least one layering of different conductivity, the porous sample being initially saturated with a first fluid, including setting the sample in a device comprising an elongate containment cell, with a first semipermeable filter permeable to the first fluid and arranged substantially in contact with a first end of the sample, and means for injecting under pressure a second fluid through a second end of the sample, electrodes applied against the sample allowing application of an electric current and detecting potential differences that appear between application points in response to application of the electrical current, establishing at least one pressure injection for the second fluid and carrying out continuous measurements of variations in complex electrical impedance of the sample at frequencies during a displacement of the first fluid, comprising:

a) carrying out measurements of the complex electrical impedance of the sample in a position where layerings are oriented substantially transverse to an electrical field created by applying the electrical current;

b) carrying out measurements of the complex electrical impedance of the sample in a position where the layerings are oriented substantially in the direction of an electrical field created by applying the electrical current; and c) determining the resistivity anisotropy.

2. A method as claimed in claim 1, wherein orientation of porous sample in relation to a fixed direction of the electrical field created by applying the electrical current is changed prior to carrying out step b).

3. A method as claimed in claim 2, wherein continuous measurements of variations in the complex electric impedance of the sample at the frequencies during drainage are performed.

4. A method as claimed in claim 1, wherein a direction of the electrical field created by applying the electric current is changed prior to carrying out step b).

5. A method as claimed in claim 4, wherein electrodes ranging in length between ¼ and ¾ of a length of the sample are used.

6. A method as claimed in claim 5, wherein continuous measurements of variations in the complex electric impedance of the sample at the frequencies during drainage are performed.

7. A method as claimed in claim 4, wherein continuous measurements of variations in the complex electric impedance of the sample at the frequencies during drainage are performed.

8. A method as claimed in claim 1, wherein electrodes ranging in length between ¼ and ¾ of a length of the sample are used.

9. A method as claimed in claim 2, wherein electrodes ranging in length between ¼ and ¾ of a length of the sample are used.

10. A method as claimed in claim 9, wherein continuous measurements of variations in the complex electric impedance of the sample at the frequencies during drainage are performed.

11. A method as claimed in claim 8, wherein continuous measurements of variations in the complex electric impedance of the sample at the frequencies during drainage are performed.

12. A method as claimed in claim 1, wherein electrodes with a length in an order of half the length of the sample are used.

13. A method as claimed in claim 12, wherein continuous measurements of variations in the complex electric impedance of the sample at the frequencies during drainage of the ample are performed.

14. A method as claimed in claim 1, wherein continuous measurements of variations in the complex electric impedance of the sample at the frequencies during draining are performed.

15. A method as claimed in claim 1, wherein continuous measurements of variations in the complex electric impedance of the sample at the frequencies during imbibition of the sample are performed.

16. A device for determining resistivity anisotropy of a porous sample traversed by at least one layering, comprising:

a containment cell for the porous sample initially saturated with a first fluid, pairs of electrodes contacting a periphery of the porous sample allowing application of an electrical current and detection of any potential difference that appears between points of the porous sample in response to application of the electrical current, electrodes connected to a device for measuring complex electrical impedance of the porous sample at frequencies during displacement of the first fluid, a first semipermeable filter permeable to the first fluid and substantially in contact with a first end of the sample, and means for injecting under pressure a second fluid through a second end of the sample, comprising a plurality of pairs of electrodes distributed over a periphery of the sample, which can be selectively connected to the device so as to position an electrical field created by applying the electrical current to the porous sample respectively in a same direction as an orientation of the at least one layering and in a direction transverse to the orientation of the at least one layering.

* * * * *